United States Patent
Liao et al.

(10) Patent No.: US 12,376,609 B2
(45) Date of Patent: Aug. 5, 2025

(54) **THERMOLABILE PIGMENTS FOR MEAT SUBSTITUTES DERIVED BY MUTATION OF THE PIGMENT OF CORAL *ECHINOPORA FORSKALIANA***

(71) Applicant: Cargill, Incorporated, Wayzata, MN (US)

(72) Inventors: Hans H. Liao, Plymouth, MN (US); Tristan Lipkie, Maple Grove, MN (US); Chris K. Miller, Andover, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 18/466,983

(22) Filed: Sep. 14, 2023

(65) Prior Publication Data

US 2024/0032569 A1   Feb. 1, 2024

Related U.S. Application Data

(63) Continuation of application No. PCT/US2022/020119, filed on Mar. 14, 2022.

(60) Provisional application No. 63/161,158, filed on Mar. 15, 2021.

(51) Int. Cl.
| | |
|---|---|
| *A23L 5/43* | (2016.01) |
| *A23J 3/16* | (2006.01) |
| *A23J 3/18* | (2006.01) |
| *A23J 3/22* | (2006.01) |
| *A23L 5/10* | (2016.01) |
| *A23L 5/42* | (2016.01) |
| *C07K 14/435* | (2006.01) |
| *C09B 61/00* | (2006.01) |

(52) U.S. Cl.
CPC . *A23L 5/43* (2016.08); *A23J 3/16* (2013.01); *A23J 3/18* (2013.01); *A23J 3/227* (2013.01); *A23L 5/10* (2016.08); *C07K 14/43595* (2013.01); *C09B 61/00* (2013.01); *A23L 5/42* (2016.08)

(58) Field of Classification Search
CPC ....... A23L 5/43; A23L 5/42; C07K 14/43595; C09B 61/00
See application file for complete search history.

(56) References Cited

U.S. PATENT DOCUMENTS

| | | | |
|---|---|---|---|
| 9,700,067 B2 | 7/2017 | Fraser | |
| 9,826,722 B2 | 11/2017 | Hudson | |
| 9,943,096 B2 | 4/2018 | Fraser | |
| 2005/0244921 A1* | 11/2005 | Tsien | C07K 14/43595 435/325 |
| 2006/0107351 A1* | 5/2006 | Karan | C07K 14/43595 536/23.6 |
| 2017/0037425 A1* | 2/2017 | Cai | C12N 15/8209 |

FOREIGN PATENT DOCUMENTS

| | | |
|---|---|---|
| EP | 1732944 B1 | 9/2012 |
| WO | WO2005100387 A1 | 10/2005 |
| WO | WO2014110539 A1 | 7/2014 |
| WO | WO2020097370 A2 | 5/2020 |
| WO | 2022197586 A1 | 9/2022 |

OTHER PUBLICATIONS

Kyriakopoulou et al., "Functionality of Ingredients and Additives in Plant-Based Meat Analogues", Mar. 12, 2021, Foods, vol. 10 (Year: 2021).*
Sha et al., "Plant protein-based alternatives of reconstructed meat: Science, technology, and challenges", 2020, Trends in Food Science & Technology, vol. 102, pp. 51-61 (Year: 2020).*
Alieva et al., "Diversity and evolution of coral fluorescent proteins." PloS one., 3(7):e2680, 12 pages, Jul. 16, 2008.
Bohrer et al., "An investigation of the formulation and nutritional composition of modern meat analogue products," Food Science and Human Wellness, 2019, 8:320-329.
Choudhury et al., "Commercialization of Plant-Based Meat Alternatives," Trends in Plant Science, Cell Press, 2020, 25(11)1055-1058.
Dominguez-Martin et al., "Engineering the orange carotenoid protein for applications in synthetic biology," Current Opinion in Structural Biology, 2019, 57:110-117.
Drobizhev et al., "Color hues in red fluorescent proteins are due to internal quadratic Stark effect." The Journal of Physical Chemistry B 113, No. 39 (2009): 12860-12864.
GenBank AF168419, "*Discosoma* sp. fluorescent protein FP583 mRNA, complete cds," Jul. 27, 2001, 2 pages.
GenBank AY059642, "*Zoanthus* sp. SAL-2001 red fluorescent protein zoanRFP mRNA, complete cds," Apr. 5, 2002, 2 pages.
GenBank DQ206379, "Montipora efflorescens red fluorescent GFP-like protein mRNA," Oct. 30, 2008, 2 pages.
GenBank DQ206380, "Porites porites red fluorescent GFP-like protein mRNA, complete cds," Oct. 30, 2008, 2 pages.
GenBank DQ206398, "Stylophora pistillata GFP-like chromoprotein mRNA, complete cds," Oct. 30, 2008, 2 pages.
GenBank EF587182, "Anemonia sulcata GFP-like chromoprotein mRNA, complete cds," May 30, 2007, 1 page.
GenBank ID AB128820, "Lithophyllon concinna mRNA for fluorescent protein, complete cds," Jul. 24, 2019, 1 page.
GenBank ID AF272711, "*Discosoma* sp. SSAL-2000 red fluorescent protein (FP593)," Sep. 26, 2000, 2 pages.

(Continued)

*Primary Examiner* — Nikki H. Dees
*Assistant Examiner* — Kelly P Kershaw

(57) ABSTRACT

Disclosed herein are pigment compositions for meat substitutes and meat substitutes including such pigment compositions. The pigment compositions include a thermolabile EforRed variant polypeptide. The pigment compositions provide a pink and/or red color to a meat substitute composition that transitions to a brown color after cooking. For example, the thermolabile EforRed variant may have a sequence at least 80% identical to SEQ ID NO:1 and include (i) an XYG chromophore tripeptide and (ii) a mutation at a position selected from the group consisting of phenylalanine (F) 68, threonine (T) 102, aspartate (D) 119, D130, alanine (A) 139, F163, F206, A214, and combinations thereof relative to SEQ ID NO:1.

29 Claims, 9 Drawing Sheets
Specification includes a Sequence Listing.

(56) References Cited

OTHER PUBLICATIONS

GenBank ID AY130757, "Entacmaea quadricolor red fluorescent protein FP611," Sep. 14, 2002, 2 pages.
GenBank ID AY296063.1, "*Carianthus* sp. DW-2003 orange fluorescent protein," Oct. 3, 2007, 2 pages.
GenBank ID AY646073.1, "Acropora millepora red fluorescent protein," Oct. 31, 2008, 2 pages.
GenBank ID EU498726.1, "Echinopora forskaliana chromo-red fluorescent GFP-like protein," Oct. 1, 2008, 2 pages.
Gross et al., "The structure of the chromophore within DsRed, a red fluorescent protein from coral." Proceedings of the National Academy of Sciences. Oct. 2, 20004; vol. 97 No. 22, pp. 11990-11995.
Hunter Lab "Hunter L, a, b Color Scale," Application Notes, Insight on Color, vol. 8, No. 9, pp. 1-4, 2008.
Khan et al., "Meat flavor precursors and factors influencing flavor precursors—A systematic review," Meat Science, 2015, 110:278-284.
Liljeruhm et al., "Engineering a palette of eukaryotic chromoproteins for bacterial synthetic biology." J Biol Eng 12, 8 (2018).
Michel et al., "Consumers' associations, perceptions and acceptance of meat and plantbased meat alternatives," Food Quality and Preference, 2021, 87:104063, 10 pages.
Miyawaki et al. "Red fluorescent proteins: chromophore formation and cellular applications," Current Opinion in Structural Biology, 2012, 22:679-688.
PDB ID 4DXM, Crystal structure of ancestral GFP-like protein, retrieved from the internet: <URL: https://www.rcsb.org/structure/4DXM>, [retrieved on Aug. 5, 2022], Feb. 27, 2013, 4 pages.
Schoenbeck et al., "Effects of pH, myoglobin form, and endpoint temperature on cooked ground beef color," Kansas Agricultural Experiment Station Research Reports, Cattlemen's Day 2000, pp. 110-112.
Van Loo et al., "Consumer preferences for farm-raised meat, lab-grown meat, and plantbased meat alternatives: Does information or brand matter?" Food Policy, 2020, 95:101931, 15 pages.
Yampolsky et al., "Synthesis and properties of the red chromophore of the green-to-red photoconvertible fluorescent protein Kaede and its analogs." Bioorganic chemistry 36, No. 2 (Apr. 2008): 96-104.

\* cited by examiner

THERMOLABILE PIGMENTS FOR MEAT SUBSTITUTES DERIVED BY MUTATION OF THE PIGMENT OF CORAL *ECHINOPORA FORSKALIANA*

CROSS-REFERENCE TO RELATED APPLICATIONS

This application is a continuation of PCT Application No. PCT/US2022/020119, filed Mar. 14, 2022, which claims the benefit of U.S. Provisional Patent Application No. 63/161,158, filed Mar. 15, 2021, each of which is incorporated by reference herein in its entirety.

REFERENCE TO A SEQUENCE LISTING SUBMITTED VIA PATENT CENTER

The content of the Sequence Listing XML file of the sequence listing named "PT-1064-US-CNT.xml" which is 9,341 bytes in size created on Aug. 8, 2023 and electronically submitted vis Patent Center herewith the application is incorporated by reference in its entirety.

BACKGROUND

Demand for plant-based meat substitutes is increasing for a variety of reasons. Many consumers prefer meat substitute options that perform most similarly to animal meat, including wanting the color of the meat substitute to be comparable to animal meat color before and after cooking. Accordingly, there is a need for a pigment that can provide color to a meat substitute that is the same or similar to that of natural animal meat. A pigment derived from natural sources that can transition in color when the meat substitute is cooked is particularly desirable.

SUMMARY

The present disclosure provides compositions comprising a thermolabile red chromogenic protein (RCP) polypeptide comprising a sequence at least 80% identical to SEQ ID NO:1 and comprising an XYG chromophore tripeptide and a mutation at a position selected from the group consisting of phenylalanine (F) 68, threonine (T) 102, aspartate (D) 119, D130, alanine (A) 139, F163, F206, A214, and combinations thereof relative to SEQ ID NO:1. The polypeptide can comprise a sequence at least 85%, at least 90%, at least 95%, at least 98%, or at least 99% identical to SEQ ID NO:1. The polypeptide can comprise a mutation selected from the group consisting of (i) a tyrosine (Y) amino acid residue at position 68; (ii) a T amino acid residue at position 214; (iii) a glycine (G) amino acid residue at position 130; (iv) a T amino acid residue at position 139; (v) a serine (S) amino acid residue at position 206; (vi) a G amino acid residue at position 119; (vii) a leucine (L) amino acid residue at position 163; (v) an A amino acid residue at position 102; and (iv) a combination thereof, all relative to SEQ ID NO:1. The polypeptide can comprise a mutation selected from the group consisting of (i) a tyrosine (Y) amino acid residue at position 68 and a T amino acid residue at position 214 relative to SEQ ID NO:1; (ii) a glycine (G) amino acid residue at position 130 and a T amino acid residue at position 139 relative to SEQ ID NO:1; (iii) a serine (S) amino acid residue at position 206 relative to SEQ ID NO:1; (iv) a G amino acid residue at position 119 and a leucine (L) amino acid residue at position 163 relative to SEQ ID NO:1; (v) an A amino acid residue at position 102 relative to SEQ ID NO:1; and (iv) a combination thereof. The polypeptide can comprise a sequence at least 80%, at least 85%, at least 90%, at least 95%, at least 98%, or at least 99% identical to the sequence of at least one of SEQ ID NOs:2-6. When the polypeptide is heated at 80° C. for 20 minutes, absorbance of light at a wavelength of 580 nm decreases relative to the absorbance prior to heating. The absorbance can be decreased by at least 20%, at least 25%, at least 30%, at least 35%, at least 40%, at least 45%, at least 50%, at least 55%, at least 60%, at least 65%, at least 70% or at least 75% relative to the absorbance prior to heating.

For example, the disclosure provides pigment compositions comprising the thermolabile RCP polypeptide. The pigment composition may be a pigment composition for a meat substitute and the pigment may comprise the thermolabile RCP polypeptide in an amount effective for increasing the red color of a raw or uncooked meat substitute. When the pigment is heated at 80° C. for 20 minutes absorbance at 580 nm is decreased relative to the absorbance at 580 nm prior to heating.

The disclosure also provides a meat substitute comprising the thermolabile RCP polypeptide and a non-meat protein. the meat substitute comprises 0.01% to 6%, 0.05% to 5%, to 3%, or 0.5% to 2% by weight of a pigment composition comprising the thermolabile RCP polypeptide. The red color of the meat substitute can decrease after cooking. The meat substitute can comprise a plant-based protein, a fungal-derived protein, an insect protein, and in vitro cultured animal cell, or combinations thereof. The non-meat protein can comprise a plant-based protein selected from the group consisting of pea protein, soy protein, corn protein, chickpea protein, and wheat protein. The non-meat protein can comprise a fungal-derived protein, for example, a fungal mycoprotein. The non-meat protein can comprise an insect protein. The meat substitute can comprise an in vitro cultured animal cell.

The disclosure further provides a cell comprising an exogenous polynucleotide encoding the thermolabile RCP polypeptide comprising a sequence at least 80% identical to SEQ ID NO:1 and comprising an XYG chromophore tripeptide and a mutation at a position selected from the group consisting of F68, T102, D119, D130, A139, F163, F206, A214, and combinations thereof, relative to SEQ ID NO:1. The cell may be a plant cell. The cell may be a fungal cell. The cell may be an animal cell, such as an insect cell or an in vitro cultured animal cell. The disclosure also provides a meat substitute comprising said cell(s).

The disclosure also provides a method for increasing the red color of a meat substitute, comprising adding a thermolabile RCP polypeptide comprising a sequence at least 80% identical to SEQ ID NO:1 and comprising an XYG chromophore tripeptide and a mutation at a position selected from the group consisting of F68, T102, D119, D130, A139, F163, F206, A214, and combinations thereof, relative to SEQ ID NO:1 to a meat substitute prior to cooking the meat substitute.

The disclosure also provides a method for decreasing red color in a cooked meat substitute, comprising: cooking a meat substitute comprising a non-meat protein and a thermolabile RCP polypeptide comprising a sequence at least 80% identical to SEQ ID NO:1 and comprising an XYG chromophore tripeptide and a mutation at a position selected from the group consisting of F68, T102, D119, D130, A139, F163, F206, A214, and combinations thereof, relative to SEQ ID NO:1, whereby the red color of the cooked meat substitute is reduced relative to red color of the meat substitute prior to cooking. When heated at 130° C. for 90 seconds, the a* value of L*a*b* colorimetry of the meat substitute decreases by at least 5, 10, 15, 20, 25, 30, 35, 40, 45, or 50%.

BRIEF DESCRIPTION OF THE FIGURES

The drawings illustrate generally, by way of example, but not by way of limitation, various aspects discussed in the present document.

DETAILED DESCRIPTION

Figure 1:
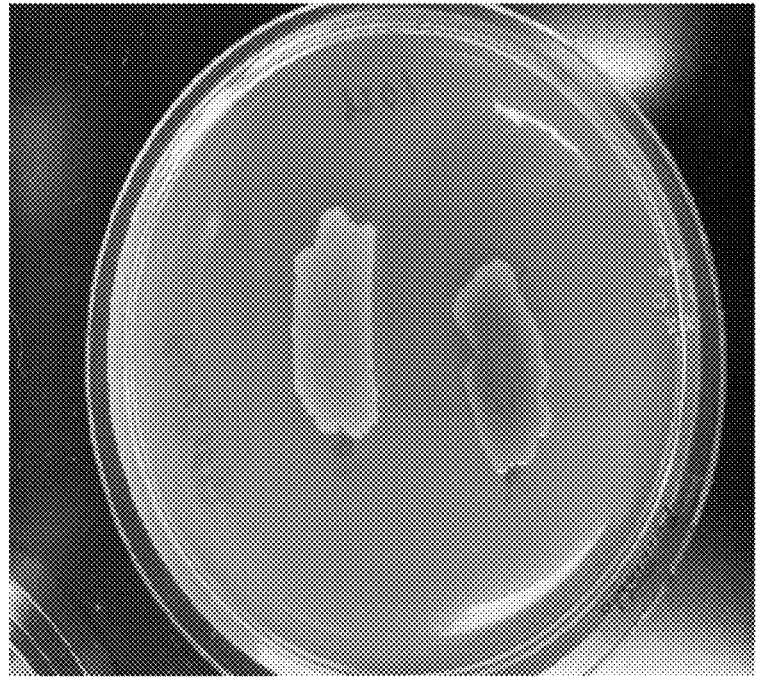
FIG. 1 is a photo of *E. coli* expressing DsRED (top streak) or EforRed (bottom streak) red chromogenic proteins.

Described herein are pigment compositions for meat substitutes that contain a thermolabile red chromogenic protein. It has been discovered that thermolabile EforRed mutants may be used in a pigment composition having a similar pink/red color to raw animal meat before cooking, but the mutations in the EforRed protein makes the pigment composition susceptible to degradation during heating. This degradation of the pigment composition causes the pigment to have a substantially reduced color or become colorless after heating. Accordingly, meat substitutes containing an effective amount of this pigment composition will transition from a red color when raw to a brown or less red color when cooked. In an aspect, the brown color occurs because the pigment composition in the meat substitute becomes at least partially colorless during heating, which allows the brown color resulting from Maillard reactions involving other components of the meat substitute to become more visible than with other pigments used for meat substitutes.

Unless defined otherwise, all technical and scientific terms used herein have the same meaning as commonly understood by one skilled in the art to which this invention belongs. As used herein, each of the following terms has the meaning associated with it as defined below.

As used herein, the terms "meat substitute" and "meat substitute composition" are used interchangeably and refer to compositions that mimic the general appearance, nutritional content, and/or taste of natural animal meat or natural animal meat compositions without containing as the majority component tissues or cells from a whole, living vertebrate animal. For example, the meat substitute may be free of, or contain as a minor component, naturally-occurring animal muscle, adipose, or satellite cells from muscle tissues harvested from a whole vertebrate animal (e.g., a cow, a sheep, a pig, a chicken, a turkey, etc.). In some aspects, the meat substitute is free of any animal cells, e.g., any in vivo derived or in vitro cultured animal cells.

The meat substitutes and meat substitute compositions described herein include non-meat proteins, plant-based proteins (e.g., pea protein, soy protein, wheat protein, chickpea protein, corn protein, and the like), fungal-based proteins (e.g., mycoproteins derived from fungi such as *Fusarium venenatum* and the like), in vitro cultured animal cells (e.g., cultured muscle cells, satellite cells, adipose cells, and the like), insect proteins, or combinations thereof. The meat substitute can comprise plant-based proteins including, but not limited to, pea protein, soy protein, wheat protein, chickpea protein, and corn protein. The meat substitute can comprise fungal based proteins including, but not limited to, mycoproteins from *Fusarium venenatum*. The meat substitute can comprise in vitro cultured animal cells including, but not limited to, muscle cells, satellite cells, and adipose cells grown, differentiated and propagated using, for example, fermentation, a bioreactor, scaffold-seeded cell culture, or other artificial methods. The meat substitute can comprise a combination of two or more of plant-based protein, fungal-based proteins, insect proteins and in vitro cultured animal cells. For example, a meat substitute may include a pea protein and a fungal mycoprotein, a soy protein and a cultured bovine muscle cell, a cultured avian adipocyte and a fungal mycoprotein, or any other combination of plant-base protein, fungal-based protein, insect proteins, and in vitro cultured animal cells.

In some aspects, the meat substitute comprises plant-based proteins, fungal-based proteins, or combinations thereof and is free of any animal-based proteins or cells. In some aspects, the meat substitute comprises plant-based proteins, fungal-based proteins, insect proteins, and combinations thereof and is free of and any vertebrate animal-based cells or proteins. In some aspects, the meat substitute comprises plant-based proteins and is free of fungal-based, insect, or animal-based cells or proteins. In some aspects, the meat substitutes comprise fungal-based proteins and is free of plant-based, insect, and animal-based cells and proteins. In aspect, the meat substitute comprises insect proteins and is free of plant-based, fungal-based, and animal-based cells and proteins. In some aspects, the meat substitute comprises in vivo cultured animal cells and is free of plant-based proteins, fungal-based proteins, insect proteins, and in vivo whole animal derived tissues, cells, and proteins.

In some aspects, the meat substitute can mimic a beef product, e.g., ground beef, steak, beef jerky, beef ribs, beef patties, beef sausages, and the like. In some aspects, the meat substitute can mimic a pork product, e.g., ground pork, pork chops, ham, smoked pork, bacon, pork sausage, pork patties, pork ribs, and the like. In some aspects, the meat substitute can mimic a chicken product, e.g., ground chicken, chicken breast, check legs, chicken thighs, chicken wings, chicken patties, chicken tenders, chicken nuggets, chicken sausage, and the like. In some aspects, the meat substitute can mimic a turkey product, e.g., ground turkey, turkey sausage, turkey patties, and the like. In some aspects, the meat substitute can mimic a shellfish product, e.g., crab, lobster, shrimp, crayfish, clams, scallops, oysters, mussels, and the like. In some aspects, the meat substitute can mimic a cured, salted, or processed meat product, e.g., charcuterie, salami, summer sausage, prosciutto, bologna, kielbasa, and the like.

As used herein, the term "non-meat protein" refers to protein sourced from plants, fungus, insects, dairy products, or in vitro cultured animal cells, and excludes in vivo vertebrate animal derived tissues, cells, or proteins. For example, non-meat proteins may include plant-based proteins, fungal-based proteins, insect proteins, milk proteins (e.g., casein and whey), proteins from in vitro cultured animal cells, or combinations thereof.

As used herein, the terms "red chromogenic protein" ("RCP") and "pink chromogenic protein" ("PCP") are used interchangeably and refer to polypeptides which, when correctly folded and, if necessary, in the presence of required co-factors, have an absorbance spectrum maximum between 450 nm and 600 nm. The absorbance spectrum maximum is also referred to in the art as a lambda max. When in an aqueous solution at a concentration of at least 0.5 mg/ml, and RCP appears red or pink when viewed by the naked eye. RCP may also be referred to in the art as "red fluorescent proteins." RCP polypeptides described include, for example, DsRED and EforRed.

The RCP polypeptides described herein are characterized by the chromophore forming tripeptide X-Y-G. Upon spontaneous cyclization and oxidate of the X-Y-G tripeptide, the chromophore includes a phenol ring derived from the Tyr residue of the tripeptide and an N-acylimine formed by desaturation of the Cα-N double bond derived from the Try backbone and formation of a double bond between Cα and Cβ of the Tyr. Chromophore formation and how the RCP chromophore differs from, for example, green and blue chromophores are known and described in the art. See, for example, Miyawaki et al. ("Red fluorescent proteins: chromophore formation and cellular applications," Current Opinion in Structural Biology, 2012, 22:679-688).

As used herein, the terms "polypeptide" and "peptide" are used interchangeably and refer to the collective primary, secondary, tertiary, and quaternary amino acid sequence and structure necessary to give the recited macromolecule its function and properties. As used herein, "enzyme" or "biosynthetic pathway enzyme" refer to a protein that catalyzes a chemical reaction. The recitation of any particular enzyme, either independently or as part of a biosynthetic pathway is understood to include the co-factors, co-enzymes, and metals necessary for the enzyme to properly function. A summary of the amino acids and their three and one letter symbols as understood in the art is presented in Table 1. The amino acid name, three letter symbol, and one letter symbol are used interchangeably herein.

TABLE 1

| Amino Acid three and one letter symbols | | |
|---|---|---|
| Amino Acid | Three letter symbol | One letter symbol |
| Alanine | Ala | A |
| Arginine | Arg | R |

TABLE 1-continued

| Amino Acid three and one letter symbols | | |
|---|---|---|
| Amino Acid | Three letter symbol | One letter symbol |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, "EforRed" refers to the RCP from the coral *Echinopora forskaliana*. GenBank ID EU498726.1. The wild-type polypeptide sequence of EforRed is provided in SEQ ID NO:1 and the MYG chromophore tripeptide is underlined.

SEQ ID NO: 1
MSVIKQVMKTKLHLEGTVNGHDFTIEGKGEGKPYEGLQHMKMTVTKGAP

LPFSVHILTPSH<u>MYG</u>SKPFNKYPADIPDYHKQSFPEGMSWERSMIFEDG

GVCTASNHSSINLQENCFIYDVKFHGVNLPPDGPVMQKTIAGWEPSVET

LYVRDGMLKSDTAMVFKLKGGGHHRVDFKTTYKAKKPVKLPEFHFVEHR

LELTKHDKDFTTWDQQEAAEGHFSPLPKALP

As used herein, the term "thermolabile RCP" refers to an RCP polypeptide that, when heated at 80° C. for 20 minutes, has a decrease in absorbance at 580 nm relative to the absorbance prior to heating. In some aspects, after heating the thermolabile RCP has an absorbance of less than 80% of the absorbance at 580 nm prior to heating. Visually, the intensity of the red or pink color of the thermolabile RCP may be reduced upon heating or the red or pink color may be completely absent following heating. Thermolabile RCPs may be wild-type, naturally occurring RCPs that show decreased red/pink color and absorbance at 580 nm upon heating. Alternatively, thermolabile RCPs may be variants of thermostable RCPs that include one or more mutation that destabilizes the RCP upon heating.

Thermolabile RCPs suitable for use in the pigments described herein include thermolabile mutants of the EforRed protein of SEQ ID NO:1. The thermolabile EforRed mutants include one or more mutations that destabilize the polypeptide such that, when heated at 80° C. for 20 minutes, the absorbance at 580 nm and the red/pink color of the polypeptide is reduced relative to the color and absorbance prior to heating. The mutation may be a substitution, deletion, or insertion. Without wishing to be bound by any particular theory, aspect, or mode of action, mutations that destabilize the chromophore or regions contributing to the structural integrity of the chromophore will produce thermolabile RCP polypeptides. See, for example, the analysis of the EforRed homology model presented in Example 4. The thermolabile RCP for use in the pigments and meat substitutes described herein can be a polypeptide with a sequence at least 80%, at least 85%, at least 90%, at least 95%, or at least 98% identical to SEQ ID NO:1 and includes an XYG chromophore tripeptide and at least one mutation relative SEQ ID NO:1 that destabilizes the polypeptide such that, when heated at 80° C. for 20 minutes absorbance at 580 nm is reduced relative to the absorbance prior to heating. The XYG chromophore tripeptide may be in a position corresponding to residues 62-64 of SEQ ID NO:1

Suitable destabilizing mutations in EforRed that from a thermolabile RCP variant include, but are not limited to, a mutation at position F68, T102, D119, D130, A139, F163, F206, A214, or combinations thereof relative to SEQ ID NO:1. The destabilizing mutation my include a substitution at one or more positions selected from the group consisting of F68, T102, D119, D130, A139, F163, F206, A214, and combinations. The destabilizing mutation may include one or more substitutes selected from F68Y, T102A, D119G, D130G, A139T, F163L, F206S, and A214T. The destabilizing mutation may include a terminator (STOP codon in the nucleotide sequence) introduced at position F163 forming a truncated EforRed variant.

The thermolabile EforRed polypeptide may include F68Y and A214T substitutions relative to SEQ ID NO:1 (SEQ ID NO:2). The thermolabile EforRed polypeptide may comprise a sequence at least 80%, at least 85%, at least 90%, at least 95%, or at least 98% identical to SEQ ID NO:2 and include the F68Y and A214T mutations relative to SEQ ID NO:1.

SEQ ID NO: 2
MSVIKQVMKTKLHLEGTVNGHDFTIEGKGEGKPYEGLQHMKMTVTKGAP

LPFSVHILTPSHMYGSKPYNKYPADIPDYHKQSFPEGMSWERSMIFEDG

GVCTASNHSSINLQENCFIYDVKFHGVNLPPDGPVMQKTIAGWEPSVET

LYVRDGMLKSDTAMVFKLKGGGHHRVDFKTTYKAKKPVKLPEFHFVEHR

LELTKHDKDFTTWDQQETAEGHFSPLPKALP

The thermolabile EforRed polypeptide may include D130G and A139T substitutions relative to SEQ ID NO:1 (SEQ ID NO:3). The thermolabile EforRed polypeptide may comprise a sequence at least 80%, at least 85%, at least 90%, at least 95%, or at least 98% identical to SEQ ID NO:3 and include the D130G and A139T substitutions relative to SEQ ID NO:1.

SEQ ID NO: 3
MSVIKQVMKTKLHLEGTVNGHDFTIEGKGEGKPYEGLQHMKMTVTKGAP

LPFSVHILTPSHMYGSKPFNKYPADIPDYHKQSFPEGMSWERSMIFEDG

GVCTASNHSSINLQENCFIYDVKFHGVNLPPGGPVMQKTITGWEPSVET

LYVRDGMLKSDTAMVFKLKGGGHHRVDFKTTYKAKKPVKLPEFHFVEHR

LELTKHDKDFTTWDQQEAAEGHFSPLPKALP

The thermolabile EforRed polypeptide may include an F206S substitution relative to SEQ ID NO:1 (SEQ ID NO:4). The thermolabile EforRed polypeptide may comprise a sequence at least 80%, at least 85%, at least 90%, at least 95%, or at least 98% identical to SEQ ID NO:4 and include the F206S substitution relative to SEQ ID NO:1.

SEQ ID NO: 4
MSVIKQVMKTKLHLEGTVNGHDFTIEGKGEGKPYEGLQHMKMTVTKGAP

LPFSVHILTPSHMYGSKPFNKYPADIPDYHKQSFPEGMSWERSMIFEDG

GVCTASNHSSINLQENCFIYDVKFHGVNLPPDGPVMQKTIAGWEPSVET

LYVRDGMLKSDTAMVFKLKGGGHHRVDFKTTYKAKKPVKLPEFHFVEHR

LELTKHDKDSTTWDQQEAAEGHFSPLPKALP

The thermolabile EforRed polypeptide may include D119G and F163L substitutions relative to SEQ ID NO:1 (SEQ ID NO:5). The thermolabile EforRed polypeptide may comprise a sequence at least 80%, at least 85%, at least 90%, at least 95%, or at least 98% identical to SEQ ID NO:5 and include the D119G and F163L substitutions relative to SEQ ID NO:1.

SEQ ID NO: 5
MSVIKQVMKTKLHLEGTVNGHDFTIEGKGEGKPYEGLQHMKMTVTKGAP

LPFSVHILTPSHMYGSKPFNKYPADIPDYHKQSFPEGMSWERSMIFEDG

GVCTASNHSSINLQENCFIYDVKFHGVNLPPDGPVMQKTIAGWEPSVET

LYVRDGMLKSDTAMVLKLKGGGHHRVDFKTTYKAKKPVKLPEFHFVEHR

LELTKHDKDFTTWDQQEAAEGHFSPLPKALP

The thermolabile EforRed polypeptide may include a T102A substitution relative SEQ ID NO:1 (SEQ ID NO:6). The thermolabile EforRed polypeptide may comprise a sequence at least 80%, at least 85%, at least 90%, at least 95%, or at least 98% identical to SEQ ID NO:6 and include the T102A substitution relative to SEQ ID NO:1.

SEQ ID NO: 6
MSVIKQVMKTKLHLEGTVNGHDFTIEGKGEGKPYEGLQHMKMTVTKGAP

LPFSVHILTPSHMYGSKPFNKYPADIPDYHKQSFPEGMSWERSMIFEDG

GVCAASNHSSINLQENCFIYGVKFHGVNLPPDGPVMQKTIAGWEPSVET

LYVRDGMLKSDTAMVFKLKGGGHHRVDFKTTYKAKKPVKLPEFHFVEHR

LELTKHDKDFTTWDQQEAAEGHFSPLPKALP

The thermolabile EforRed polypeptide may include a terminator at position F163 relative to SEQ ID NO:1 (SEQ ID NO:7). The EforRed polypeptide may exclude at least residues 163-227 of SEQ ID NO:1 (SEQ ID NO:7). The thermolabile EforRed polypeptide may comprise a sequence at least 80%, at least 85%, at least 90%, at least 95%, or at least 98% identical to SEQ ID NO:7 and excludes at least residues 163-227 of SEQ ID NO:1.

SEQ ID NO: 7
MSVIKQVMKTKLHLEGTVNGHDFTIEGKGEGKPYEGLQHMKMTVTKGAP

LPFSVHILTPSHMYGSKPFNKYPADIPDYHKQSFPEGMSWERSMIFEDG

GVCTASNHSSINLQENCFIYDVKFHGVNLPPDGPVMQKTIAGWEPSVET

LYVRDGMLKSDTAMV

Variants or sequences having substantial identity or homology with the polypeptides described herein can be utilized in the practice of the disclosed pigments, compositions, and methods. Such sequences can be referred to as variants or modified sequences. That is, a polypeptide sequence can be modified yet still retain the ability to exhibit the desired activity. Generally, the variant or modified sequence may include or greater than about 45%, 45%, 50%, 55%, 60%, 65%, 70%, 75%, 80%, 85%, 90%, or 95% sequence identity with the wild-type, naturally occurring polypeptide sequence, or with a variant polypeptide as described herein.

As used herein, the phrases "% sequence identity," "% identity," and "percent identity," are used interchangeably and refer to the percentage of residue matches between at least two amino acid sequences or at least two nucleic acid sequences aligned using a standardized algorithm. Methods of amino acid and nucleic acid sequence alignment are well-known. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, -2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

Polypeptide or polynucleotide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The polypeptides disclosed herein may include "variant" polypeptides, "mutants," and "derivatives thereof." As used herein the term "wild-type" is a term of the art understood by skilled persons and means the typical form of a polypeptide as it occurs in nature as distinguished from variant or mutant forms. As used herein, a 37 variant, "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule.

The amino acid sequences of the polypeptide variants, mutants, derivatives, or fragments as contemplated herein may include conservative amino acid substitutions relative to a reference amino acid sequence. For example, a variant, mutant, derivative, or fragment polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge and/or hydrophobicity of the molecule at the site of the substitution, and/or (c) the bulk of the side chain.

As used herein, terms "polynucleotide," "polynucleotide sequence," and "nucleic acid sequence," and "nucleic acid," are used interchangeably and refer to a sequence of nucleotides or any fragment thereof. There phrases also refer to DNA or RNA of natural or synthetic origin, which may be single-stranded or double-stranded and may represent the sense or the antisense strand. The DNA polynucleotides may be a cDNA or a genomic DNA sequence.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

Those of skill in the art understand the degeneracy of the genetic code and that a variety of polynucleotides can encode the same polypeptide. In some aspects, the polynucleotides (i.e., polynucleotides encoding an EforRed polypeptide) may be codon-optimized for expression in a particular cell including, without limitation, a plant cell, bacterial cell, fungal cell, or animal cell. While polypeptides encoded by polynucleotide sequences found in coral are disclosed herein any polynucleotide sequences may be used which encodes a desired form of the polypeptides described herein. Thus, non-naturally occurring sequences may be used. These may be desirable, for example, to enhance expression in heterologous expression systems of polypeptides or proteins. Computer programs for generating degenerate coding sequences are available and can be used for this purpose. Pencil, paper, the genetic code, and a human hand can also be used to generate degenerate coding sequences.

Also provided herein are polynucleotides encoding a thermolabile EforRed polypeptide. The polynucleotide may encode any of the thermolabile EforRed polypeptides described herein, for example, the polynucleotide may encode a polypeptide at least 80%, at least 85%, at least 90%, at least 95%, or at least 98% identical to SEQ ID NO:1 that includes a mutation at position F68, T102, D119, D130, A139, F163, F206, A214, or combinations thereof relative to SEQ ID NO:1.

The polypeptides described herein may be provided as part of a construct. As used herein, the term "construct" refers to recombinant polynucleotides including, without limitation, DNA and RNA, which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome editing technologies. Constructs may also include recombinant polynucleotides created using, for example, recombinant DNA methodologies. The construct may be a vector including a promoter operably linked to the polynucleotide encoding the thermolabile EforRed polypeptide. As used herein, the term "vector" refers to a polynucleotide capable of transporting another polynucleotide to which it has been linked. The vector may be a plasmid, which refers to a circular double-stranded DNA loop into which additional DNA segments may be integrated.

Cells including any of the polynucleotides, constructs, or vectors described herein are also provided. The cell may be a procaryotic cell or a eukaryotic cell. Suitable procaryotic cells include bacteria cell, for example, *Escherichia coli* and *Bacillus subtilis* cells. Suitable eukaryotic cells include, but are not limited to, fungal cells, plant cells, and animal cells. Suitable fungal cells include, but are not limited to, *Fusarium venenatum, Pichia pastoris, Saccharomyces cerevisiae, Kluyveromyces lactis, Yarrowia lipolytica, Trichomderma reesei, Issatchenkia orientalis*, and *Aspergillus niger* cells. Suitable plant cells include, but are not limited to, a pea cell (*Pisum sativum*), a corn cell (*Zea mays*), a soybean cell (*Glycine max*), and a wheat cell (*Triticum* sp.). Suitable animal cells include, but are not limited to, muscle cells (e.g., myocytes, myoblasts, myosatellite, and satellite cells) and fat cells (e.g., adipocytes or adipocyte progenitor cells such as mesenchymal stem cells). Suitable animal cells may be mammalian (e.g., bovine, porcine, and ovine), avian (e.g., poultry), crustacean (e.g., shrimp, lobster, and crab), mollusk (e.g., clam, mussel, scallop, and oyster) or insect cells. In some aspects, the cell is an edible mushroom cell, which refers to a mushroom that is safe for human consumption. For example, the edible mushroom cell can be a *Fusarium venenatum, Agaricus bisporus, Lentinula edodes*, or *Volvariella volvacea* cell.

Described herein are pigment compositions containing a thermolabile RCP, and meat substitutes including such pigment compositions. The pigment compositions disclosed herein can be used to provide color to a meat substitute that is similar to the color of natural animal meat when raw. Further, these pigment compositions change color upon heating and can provide an overall color change to the entire meat substitute composition that mimics the effects of cooking on natural animal meat. In an aspect, the pigment composition provides a pink and/or red color to raw, uncooked meat substitute that transitions to a brown, white, colorless, or less red color after cooking the meat substitute.

The pigment composition itself loses its pink or red color as it is cooked due to degradation and may become colorless if enough degradation occurs. Accordingly, the brown color of a cooked meat substitute is not necessarily due to the pigment composition turning brown in color, but instead due to the pigment composition losing its reddish color. The degraded pigment composition in the cooked meat substitute no longer masks the other colors of the meat substitute and the brown colors associated with Maillard reactions in the meat substitute become more apparent.

The redness of the pigment composition is reduced substantially or eliminated when heated to a temperature within a range typically used for cooking meat. The pigment composition changes from a pink and/or red color to a less-pink/red color or becomes substantially colorless when heated at 80° C. for 20 minutes. The pigment composition can be used to change the color of a meat substitute from a pink and/or red color to a brown color and/or less pink/red color, as exhibited by heating a meat substitute including the pigment composition at 80° C. for 20 minutes.

The changes in color of a pigment composition sample can be measured using a Hunter Colorimeter and reported as a relative percent change in visible light absorbance after heating as compared to the sample prior to heating. When the thermolabile EforRed RCP, the pigment composition, or the meat substitute is heated on a hot plate at 130° C. for 90 seconds, the a* value of L*a*b* colorimetry of the pigment composition decreases relative to the a* value prior to heating. The a* value may decrease by at least 5%, at least 10%, at least 15%, at least 20%, at least 25%, at least 30%, at least 35%, at least 40%, at least 45%, or at least 50%. Likewise, when the thermolabile EforRed RCP, the pigment composition, or the meat substitute is heated at 80° C. for minutes the absorbance of light at a wavelength of 580 nm is decreased relative to the absorbance prior to heating. The absorbance at 580 nm may decrease by at least 5%, at least 10%, at least 15%, at least 20%, at least 25%, at least 30%, at least 35%, at least 40%, at least 45%, or at least 50%.

The pigment compositions described herein include a thermolabile variant of the EforRed RCP. The thermolabile variant of EforRed in the pigment composition may be any thermolabile valiant described herein. For example, the pigment composition may include a polypeptide with a sequence at least 80%, at least 85%, at least 90%, at least 95%, or at least 98% identical to SEQ ID NO:1 and includes at least one mutation relative SEQ ID NO:1 that destabilizes the polypeptide such that, when heated at 80° C. for 20 minutes absorbance at 580 nm is reduced relative to the absorbance prior to heating. The pigment compositions may include a polypeptide with a sequence at least 80%, at least 85%, at least 90%, at least 95%, or at least 98% identical to SEQ ID NO:1 with a mutation in at least one position selected from the group consisting of F68, T102, D119, D130, A139, F163, F206, A214, or combinations thereof relative to SEQ ID NO:1. The pigment compositions may include a polypeptide with a sequence at least 80%, at least 85%, at least 90%, at least 95%, or at least 98% identical to SEQ ID NO:1 that includes a substitution selected from F68Y, T102A, D119G, D130G, A139T, F163L, F206S, A214T, and combinations thereof relative to SEQ ID NO:1. The pigment compositions may include a polypeptide with a sequence at least 80%, at least 85%, at least 90%, at least 95%, or at least 98% identical to SEQ ID NO:2 and including the F68Y and A214T mutations relative to SEQ ID NO:1. The pigment compositions may include a polypeptide with a sequence at least 80%, at least 85%, at least 90%, at least 95%, or at least 98% identical to SEQ ID NO:3 and including the D130G and A139T substitutions relative to SEQ ID NO:1. The pigment compositions include a polypeptide with a sequence at least 80%, at least 85%, at least 90%, at least 95%, or at least 98% identical to SEQ ID NO:4 and including the F206S substitution relative to SEQ ID NO:1. The pigment compositions may include a polypeptide with a sequence at least 80%, at least 85%, at least 90%, at least 95%, or at least 98% identical to SEQ ID NO:5 and including the D119G and F163L substitutions relative to SEQ ID NO:1. The pigment compositions may include a polypeptide at least 80%, at least 85%, at least 90%, at least 95%, or at least 98% identical to SEQ ID NO:6 and including the T102A substitution relative to SEQ ID NO:1. The pigment compositions may include a polypeptide with a sequence at least 80%, at least 85%, at least 90%, at least 95%, or at least 98% identical to SEQ ID NO:7 and excluding at least residues 163-227 of SEQ ID NO:1.

The pigment composition can be included in a meat substitute at a level that provides increased or improved pink and/or red color in the meat substitute, while also providing increased or improved brown color in the meat substitute after cooking. In an aspect, the pigment composition is used at a level of at least 0.01%, 0.05%, 0.1%, 0.2%, 0.3%, 0.4%, 0.5%, 1.0%, 1.25%, or 1.5% on a wet (total) weight basis in a meat substitute composition. The pigment composition may be used at a level in the range of 0.01% to 6%, 0.05% to 5%, 0.1% to 3%, or to 2% by weight in a meat substitute composition.

The pigment composition may additionally include a carrier or a diluent. The pigment composition may also include a blend of the RCP polypeptide with another color or pigment. For example, the pigment composition may include the RCP polypeptide and a fruit or vegetable extract-based pigment composition.

The pigment composition described herein can be used as a pigment in any meat substitute composition. An exemplary, but non-limiting, meat substitute composition is a composition which comprises: plant protein (e.g., textured pea protein and/or pea protein), water, vegetable oil, flavor ingredients, salt, sugar, binders, and the pigment composition described herein. The pigment composition described herein can also be used in food applications other than meat substitutes.

Meat substitutes described herein may include one or more cells comprising an exogenous polynucleotide encoding a thermolabile EforRed RCP as described herein. For example, the meat substitutes may include a fungal, plant, or animal cell as described herein comprising an exogenous polynucleotide encoding a thermolabile EforRed protein described herein.

Also provided herein is a method for increasing the red color of a meat substitute. The method for increasing the red color of a meat substitute includes adding a thermolabile RCP polypeptide to a meat substitute prior to cooking the meat substitute, wherein the red color of the meat substitute is increase relative to the meat substitute without the thermolabile RCP polypeptide. The method may also include adding a thermolabile RCP polypeptide to a non-meat protein to form a meat substitute with increased red color relative to the non-meat protein without the RCP polypeptide. The thermolabile RCP polypeptide may be any thermolabile RCP polypeptide as described herein. For example, the thermolabile RCP polypeptide to be added to the meat substitute may comprise a sequence at least 80% identical to SEQ ID NO:1 and comprise a mutation at a position selected from the group consisting of F68, T102, D119, D130, A139, F163, F206, A214, and combinations thereof, relative to SEQ ID NO:1.

Also provided is a method for decreasing red color in a cooked meat substitute. The method for decreasing the red color in a cooked meat substitute includes cooking a meat substitute comprising a non-meat protein and a thermolabile RCP, whereby red color of the cooked meat substitute is reduced relative to the meat substitute prior to cooking. The thermolabile RCP polypeptide may be any thermolabile RCP polypeptide as described herein. For example, the thermolabile RCP polypeptide to be added to the meat substitute may comprise a sequence at least 80% identical to SEQ ID NO:1 and comprise a mutation at a position selected from the group consisting of F68, T102, D119, D130, A139, F163, F206, A214, and combinations thereof, relative to SEQ ID NO:1.

EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather should be construed to encompass any and all variations which become evident as a result of the teaching provided herein.

Example 1: EforRed and DsRed Thermostability

Figure 2:
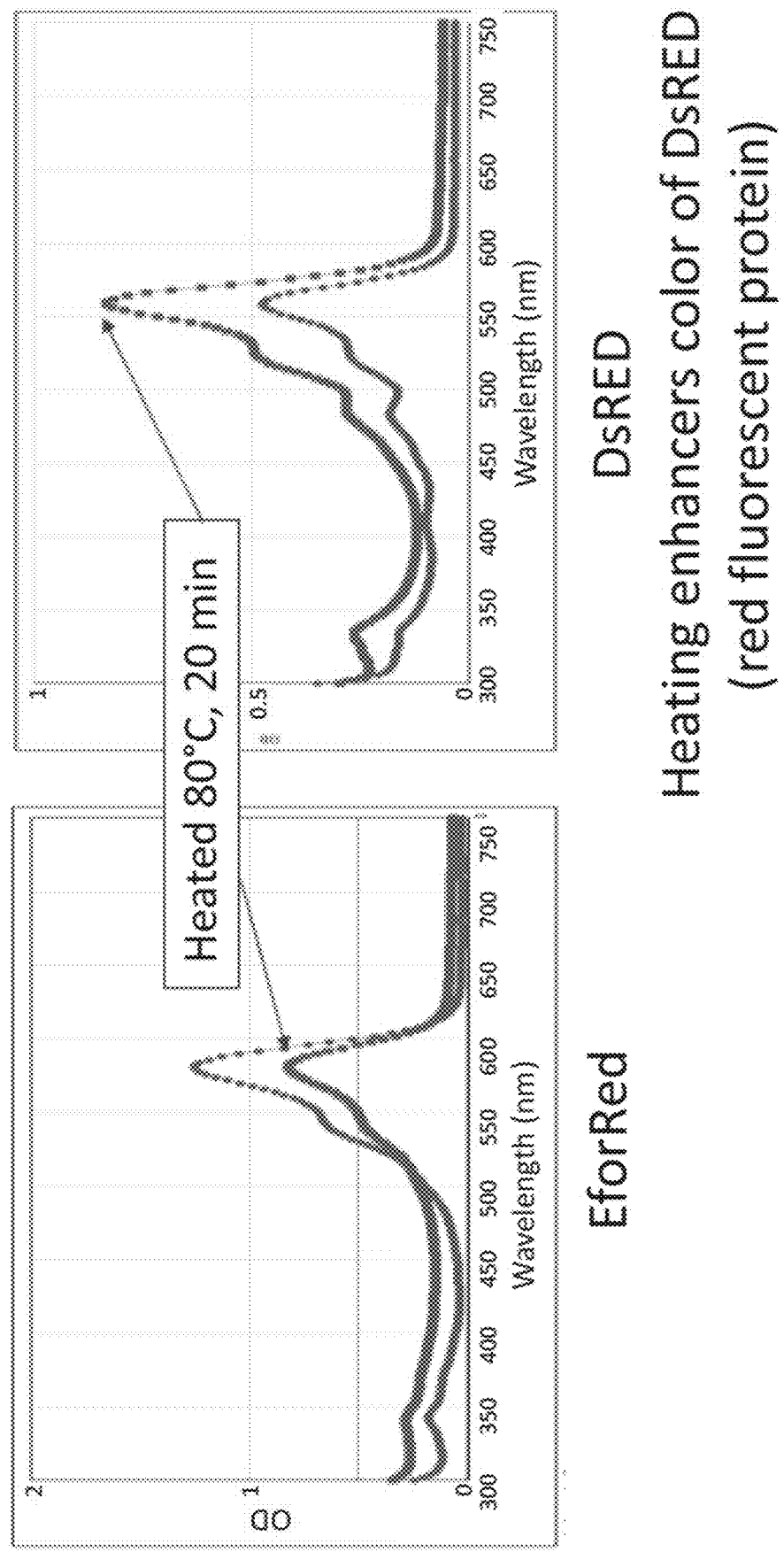
FIG. 2 shows the visible wavelength absorbance data of DsRED (right) and EforRed (left) before and after heating at 80° C. for 20 minutes.

EforRed was expressed in *E. coli* cells using a His6 tag with a protease cleavage site (MGSSHHHHHHSSGLVPRGSH, SEQ ID NO:8) on the N-terminus of the EforRed sequence of SEQ ID NO:1. Both red chromogenic proteins EforRed and DsRed are red/pink in color (FIG. 1) and demonstrate the corresponding absorbance peak at the 580 nm wavelength. Upon heating at ° C. for 20 minutes, both EforRed and DsRed remained stable, maintaining the absorbance peak and 580 nm, with DsRed showing an increase in absorbance at 580 nm following heating (FIG. 2).

Example 2: EforRed Mutagenesis and Thermal Stability

Figure 3:
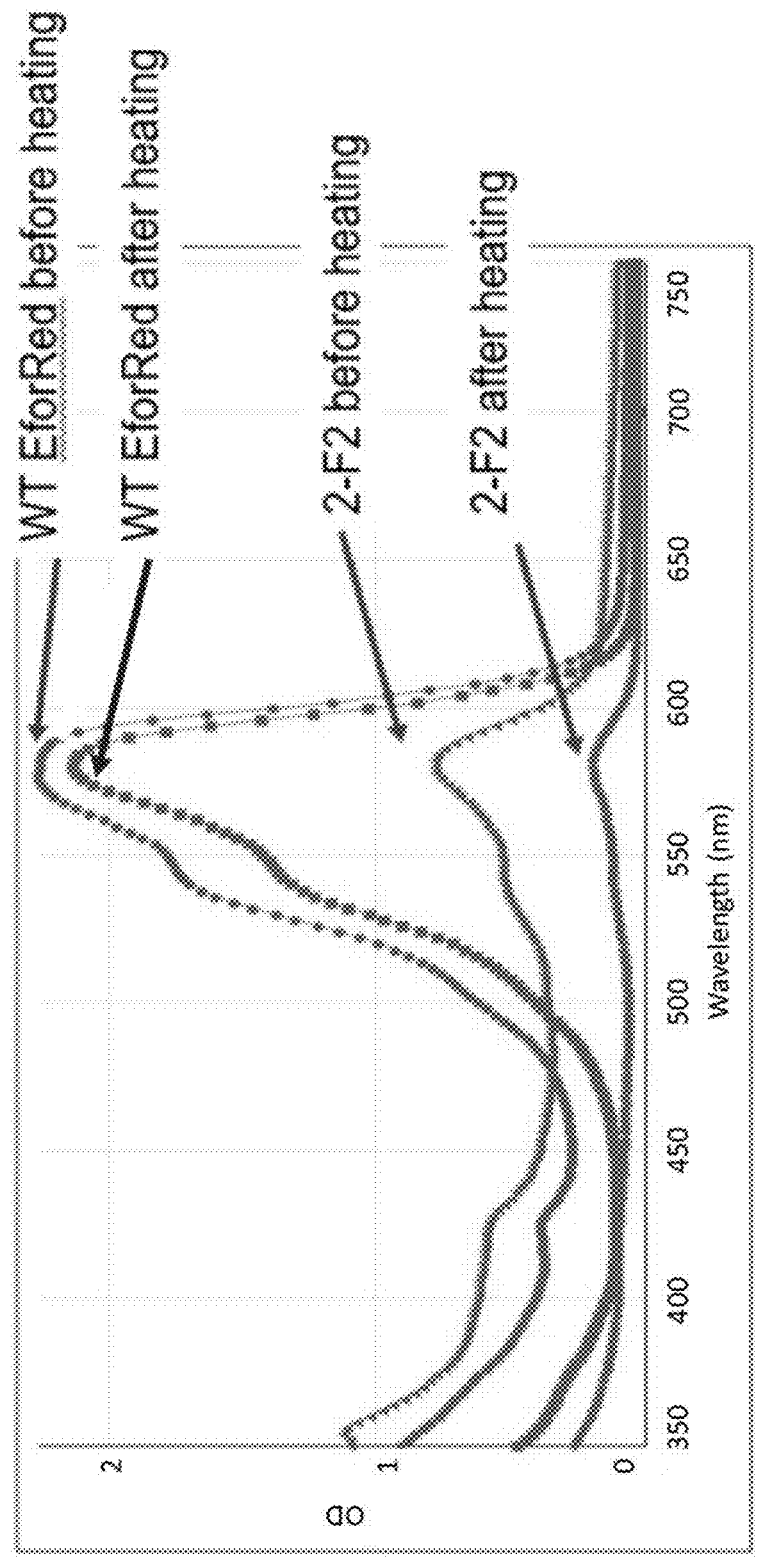
FIG. 3 shows the visible wavelength absorbance data for wild-type EforRed and the 2-F2 mutant EforRed before and after heating at 80° C. for 20 minutes.

A library of EforRed mutants was generated using error-prone PCR. The error-prone PCR on the wild-type EforRed sequence, which included a region coding for the His6 tag and protease cleavage site of SEQ ID NO:8, was carried out with a nonproofreading DNA polymerase in the presence of $Mn^{2+}$, the resulting polynucleotides were transformed into *E. coli*, and resulting red *E. coli* colonies were selected for further screening. The selected colonies were grown up on in 96-well liquid cultures, cells were lysed, and the lysate supernatant was removed from the cell debris. The absorbance of the lysate supernatant at 580 nm was measured before and after heating at 80° C. for 20 min. Lysates that demonstrated a decrease in A580 following heating were repeated in ml cultures. Results for the lysates from the 50 ml cultures, along with characterization of the destabilizing mutation relative to SEQ ID NO:1, are shown in Table 2 and absorbance curves for wild-type and 2-F2 mutant EforRed are shown in FIG. 3. "% absorbance at 580 nm after heating" in Table 2 is the % absorbance at 580 nm after heating compared to the lysate prior to heating.

TABLE 2

| 50 ml lysate thermal stability | | | | |
|---|---|---|---|---|
| Lysate | Initial A580 | A580 after heating | % absorbance at 580 nm after heating | Mutation |
| 1-C1 | 1.506 | 0.913 | 61% | D130G and A139T |
| 1-G2 | 0.080 | 0.035 | 44% | |
| 1-F7 | 1.673 | 1.285 | 77% | Terminator at F163 |
| 1-H12 (wild-type) | 2.252 | 2.129 | 95% | |
| 2-D5 | 0.197 | 0.094 | 48% | |
| 2-F2 | 0.788 | 0.189 | 24% | F68Y and A214T |
| 2-G11 | 0.353 | 0.219 | 62% | F206S |
| 2-H2* | 0.754 | 0.527 | 70% | (i) D119G and F163L (ii) T102A |

*Two EforRed mutants identified in the 2-H2 lysate

Example 3: Application Test of EforRed Mutant Pigment Compositions

Figure 4:
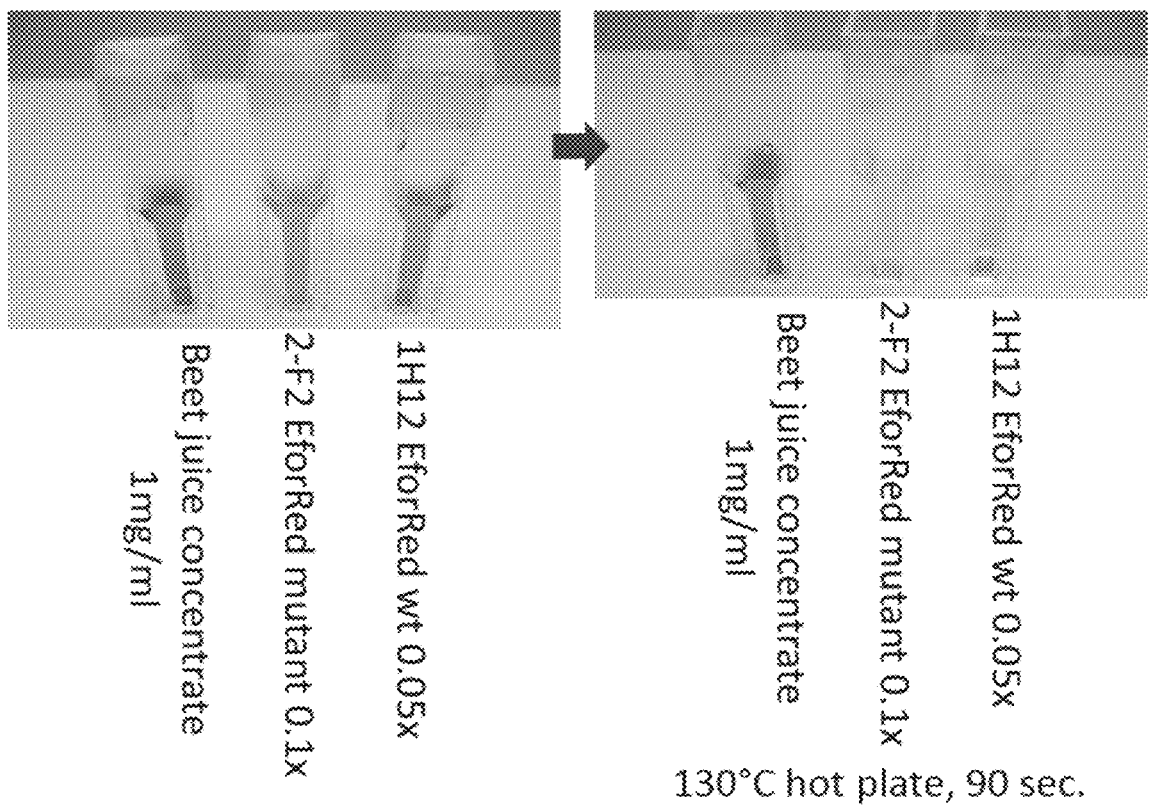
FIG. 4 shows a series of photos of beet juice concentrate, the 2-F2 EforRed mutant, and wild-type EforRed in water before (top, right) and after (top, left) heating at 130° C. for 90 seconds. Also shown is visible wavelength absorbance data (bottom) for the pictured samples.
Figure 4:
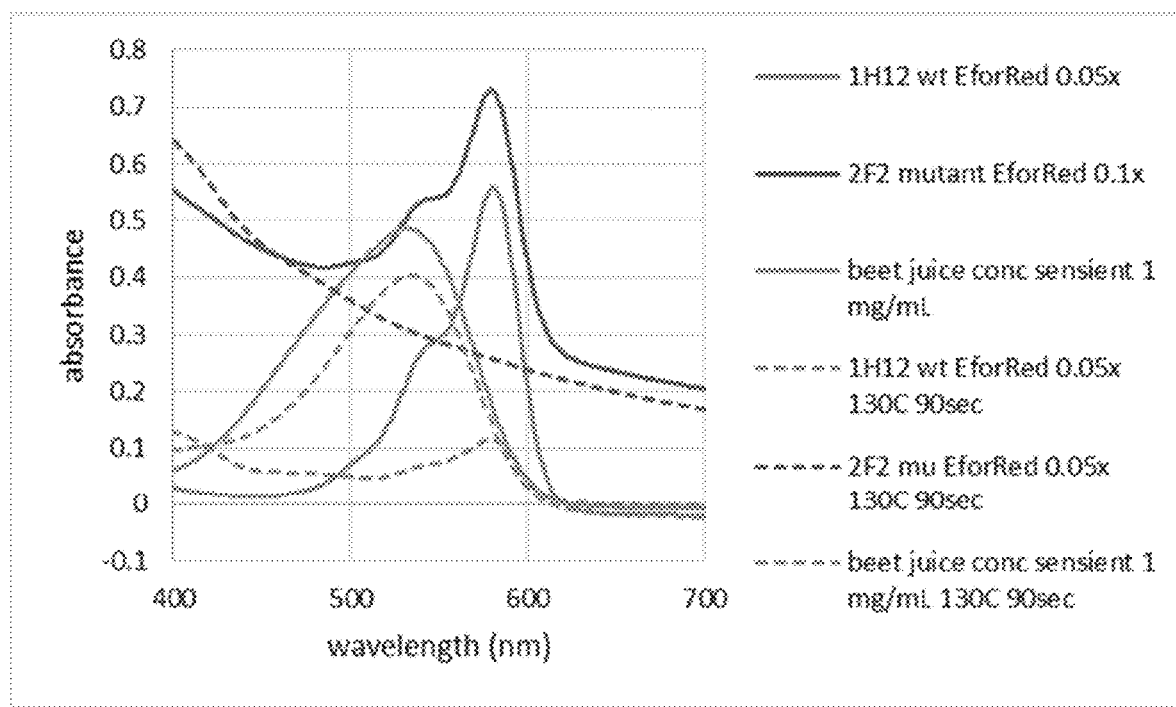

For testing in the meat substitute composition, wild-type EforRed lysate was diluted by 0.5× to match the intensity of the 2-F2 mutant lysate. Color intensity loss from the 2-F2 mutant was faster and greater than from either wild-type EforRed or the red beet juice control. These results are demonstrated in FIG. 4.

Figure 5:
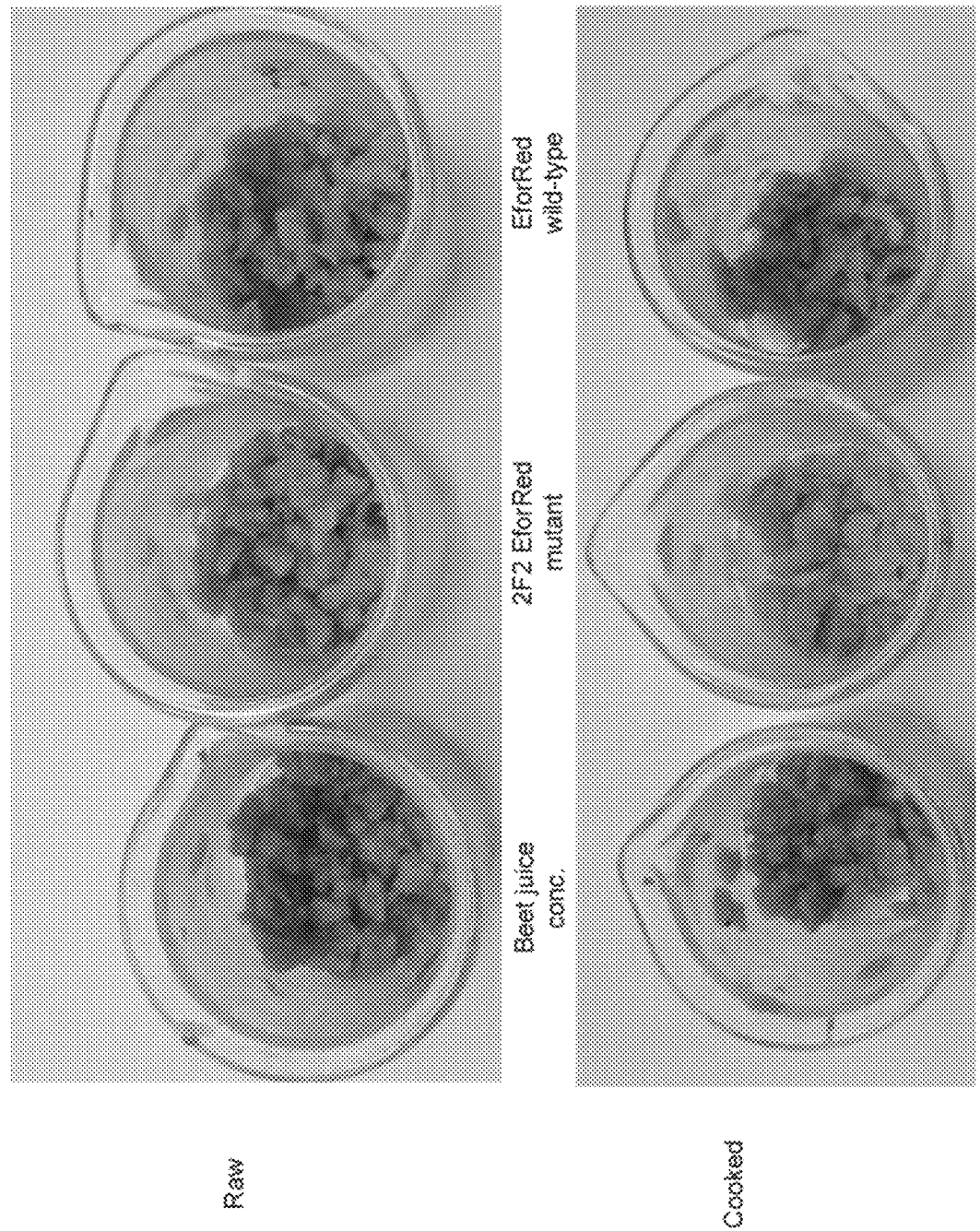
FIG. 5 shows a series of photos of a small lab scale meat substitute application incorporating a beet juice concentrate, a 2-F2 EforRed mutant, and an EforRed pigment before (top, "raw") and after (bottom, "cooked") heating on a hot plate set at 130° for 90 seconds.

In a small-scale application model of a meat substitute composition, each of the beet juice concentrate, the EforRed 2-F2 mutant, and the wild-type EforRed pigments increased the red color of the raw meat substitute composition (FIG. 5). Upon heating on a hot plate at 130° C. for 90 seconds to simulate cooking on a skillet (see "Cooked" in FIG. 5), the red color of the EforRed 2-F2 mutant pigment was reduced while the beet juice and wild-type EforRed pigments retained the red color. Hunter colorimetry data for each of meat substitute pigmentations are reported in Table 3.

Figure 6:
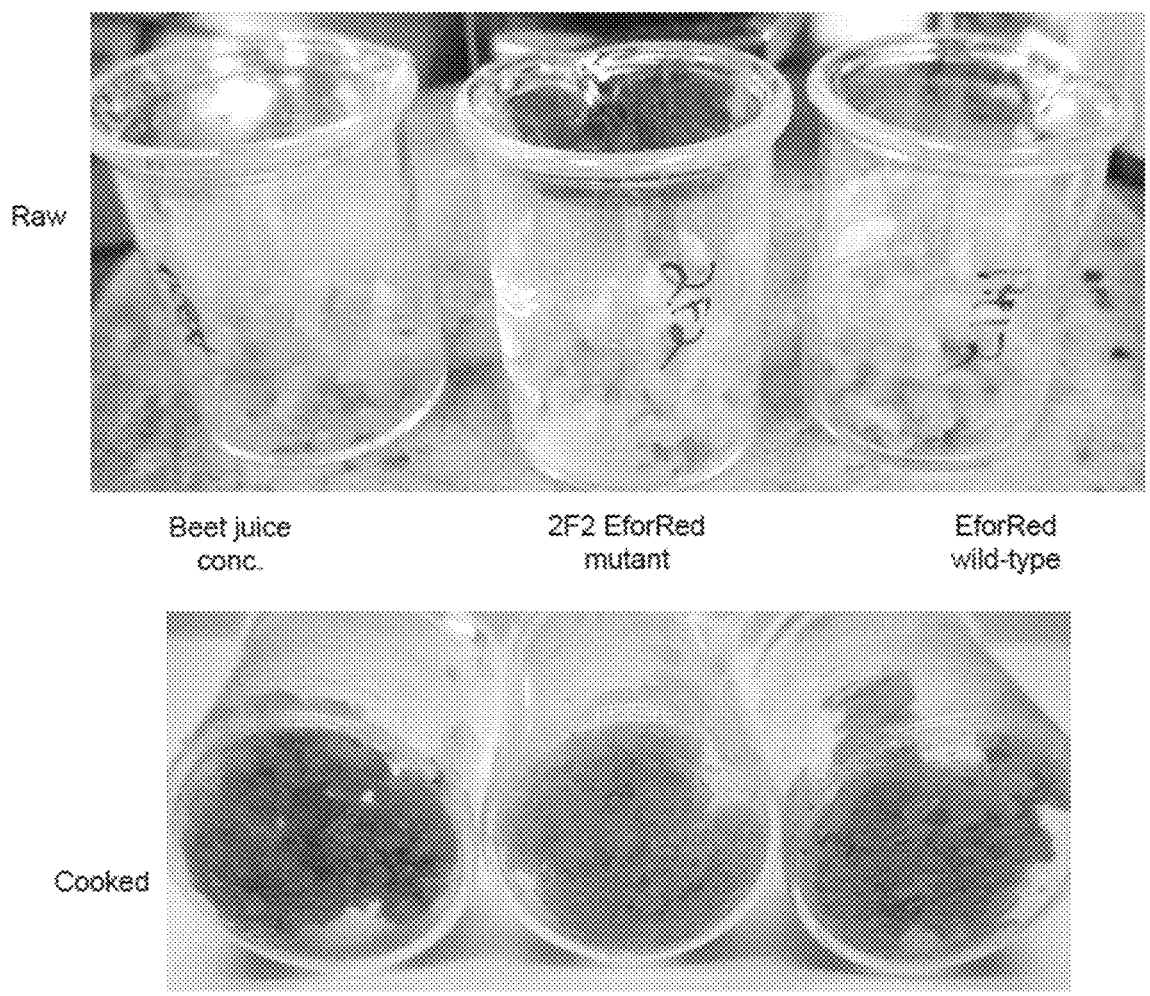
FIG. 6 shows a series of photos of a tiny patty meat substitute incorporating a beet juice concentrate, a 2-F2 EforRed mutant, and an EforRed pigment before (top, "raw") and after (bottom, "cooked") heating at 80° C. for 20 minutes.

The color change in the small-scale application model occurred from the surface towards the interior, mimicking "rare" internal appearance observed when the cooking animal-derived ground beef. Other pigments showed no fading (e.g., beet juice concentrate) or consistent fading (e.g., deglycosylated beet juice, not shown) throughout the entire product (FIG. 6).

Figure 7:
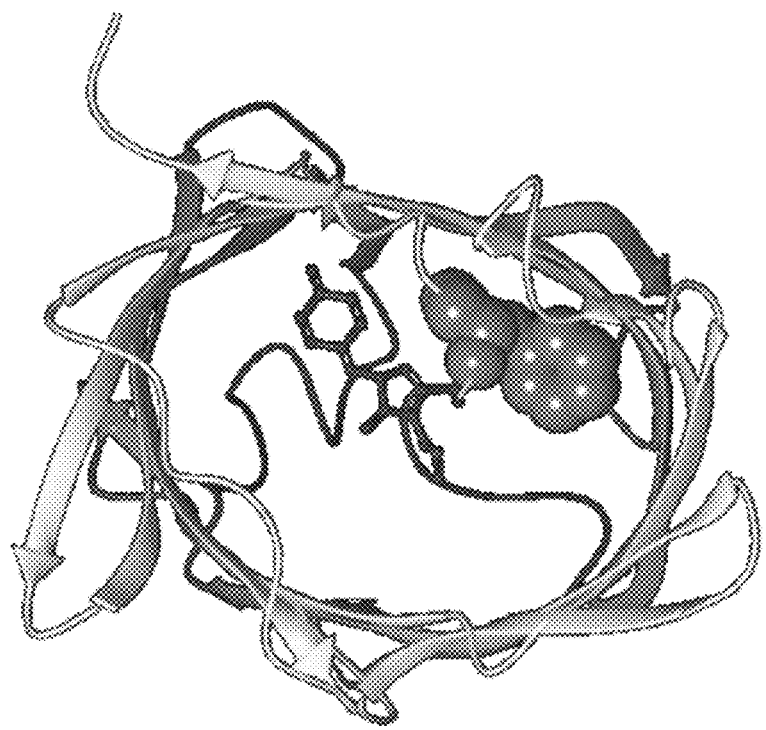
FIG. 7 shows a model of the EforRed structure. Phenylalanine 68 is shown as a space filling model within the interior of the β-barrel fold, shown in a ribbon diagram. The EforRed chromophore, formed from the MYG tripeptide, is shown as a stick model.
Figure 8:
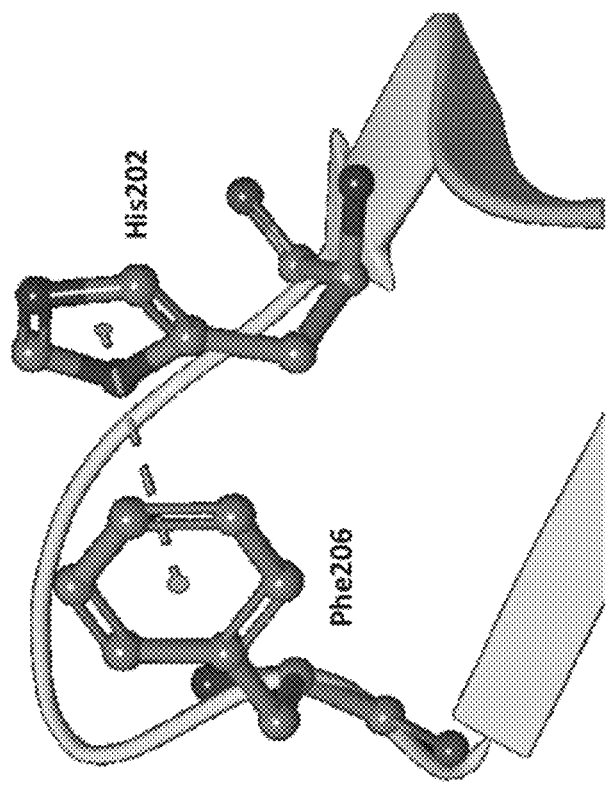
FIG. 8 shows the pi-pi stacking interactions between phenylalanine 206 and histidine 202 in a model of the EforRed structure. F206 and $H_2O_2$ shown as a ball-and-stick model, and the backbone is shown as a ribbon diagram.

The 2-F2 lysate contained a mutant EforRed polypeptide with F68Y and A214T substitutions. As demonstrated in FIG. 7, amino acid position 68 (shown as a space-filling model) is within the β-barrel fold (shown as a ribbon structure) and the phenylalanine in this position is tightly packed within the core of the β-barrel. The substitution to tyrosine in this position adds the bulk of the additional hydroxyl group destabilizing the β-barrel fold. The calculations show that the tyrosine substitution in position 68 destabilizes the protein and slightly increases binding affinity of the monomer to the other monomers in the tetramer. In this model, alanine 214 of EforRed is located at the homodimer interface and the substitution to threonine increases the size of the side chain and introduces a hydroxyl group destabilizing the homodimer interface. However, A214 is on the β-barrel and interacts with the flexible C-terminal tail of the protein, which is likely is many different positions depending on protein folding and crystal packing. Due to this variability and flexibility, the calculations presented in Table 4 for the 2-F2 lysate mutant were

TABLE 3

Hunter colorimetry of pigment containing meat substitutes

| Pigment | raw | | | | | cooked | | | | | delta | | | | |
| --- | --- | --- | --- | --- | --- | --- | --- | --- | --- | --- | --- | --- | --- | --- | --- |
| | L* | a* | b* | C* | h | L* | a* | b* | C* | h | L* | a* | b* | C* | h |
| EforRed Wild-Type | 47.7 | 20.3 | 4.5 | 20.7 | 12.4 | 48.1 | 11.0 | 12.4 | 16.6 | 48.5 | 0.5 | −9.3 | 7.9 | −4.2 | 36.1 |
| 2-F2 EforRed mutant | 49.7 | 20.0 | 7.7 | 21.4 | 21.0 | 55.1 | 5.6 | 22.5 | 23.1 | 76.1 | 5.4 | −14.4 | 14.8 | 1.7 | 55.1 |
| Beet Juice Concentrate | 46.0 | 22.3 | 8.0 | 23.7 | 19.7 | 43.4 | 20.3 | 12.9 | 24.1 | 32.3 | −2.7 | −2.0 | 4.9 | 0.4 | 12.6 |

Example 4: EforRed Homology Model and Stability Predictions

A homology model of the EforRed protein was built using the x-ray crystal structure of ancestral GFP-like protein (PDB ID 4DXM). For each of mutant EforRed polypeptides identified in the lysates outlined in Table 2, positional analysis was carried out to evaluate the potential effects of the amino acid side chain substitutions on the stability of the EforRed polypeptide. Likewise, binding affinity and stability calculations were performed using the homology model and the mutations noted in Table 4. Δ Affinity is a measure of the change in the binding affinity of one monomer for the other monomers of the tetramer as a result of the recited mutation(s). A negative Δ Affinity value indicates that the mutation binds better than the wild-type protein. Δ Stability is a measure of the change in stability of the protein as a result of the recited mutation(s). A negative Δ Stability indicates that the mutant is more stable than the wild-type protein. The BioLuminate application in the Schrodinger platform was used to build the homology models and to calculate estimated changes in binding affinity and stability values.

TABLE 4

| Lysate | Mutations | Δ Affinity (kcal/mol) | Δ Stability (kcal/mol) |
| --- | --- | --- | --- |
| 2-F2 | F68Y* | 0.15 | 3.7 |
| 1-C1 | D130G; A139T | −6.13 | −5.62 |
| 2-G11 | F206S | −0.55 | 47.35 |
| 2-H2 | D119G; F163L | −2.3 | 22.63 |
| 2-H2 | T102A | 17.11 | 32.32 |

*Only the F86Y mutation was used to calculate the affinity and stability changes in the EforRed mutant of the 2-F2 lysate due to the variability and flexibility in the C-terminal region of EforRed.

done with only the F68Y mutation and does not include the A214T mutation. The homology model energy calculations estimate that the F68Y mutation destabilizes the EforRed polypeptide (3.7 kcal/mol). While the calculation estimates that the mutation may increase the affinity of the monomer for binding in the homotetramer (−0.15 kcal/mol), this is likely not enough to make up for the monomer destabilization.

The 1-C1 lysate contained a mutant EforRed polypeptide with D130G and A139T substitutions. The aspartic acid in position 130 hydrogen bonds with another monomer in the EforRed homotetramer. This intermonomer hydrogen bond is lost when the glycine residue is present in position 130, which destabilizes the homotetramer. The alanine in position 139 is near a loop within the monomer. Based on the structural analysis alone, it's unclear how the threonine substitution at this position destabilizes the EforRed tertiary or quaternary structure. The homology model calculations in Table 4 suggest these two mutations may increase the affinity of the monomer for the other monomers in the tetramer (−6.13 kcal/mol) and they may be stabilizing the monomer (−5.62 kcal/mol). However, data presented in Example 2 clearly demonstrates that the D130G and A139T substitutions result in a thermolabile EforRed polypeptide. The homology model calculations alone are not sufficient to account for the structural contributions of these substitutions to the instability upon heating.

The 1-F7 lysate contained a truncated EforRed polypeptide with a terminator introduced at position 163. Amino acids 163-227 of the EforRed polypeptide account for portions of the homodimer and homotetramer interface. Loss of these residues in the truncated mutant will result in a mutant with destabilized dimeric and tetrameric interactions as well as reduced stability of the overall β-barrel fold.

The 2-G11 lysate contained a mutant EforRed polypeptide with an F206S substitution. As demonstrated in FIG. 9, the phenylalanine at position 206 is involved in pi-pi stacking interactions (shown as a dotted line) with histidine 202. This pi-pi stacking is lost upon substitution to serine in this position, disrupting the stability of EforRed. The homology model energy calculations in Table 4 estimate that the F206S substitution significantly destabilizes the protein (47.35 kcal/mol). While the calculations also estimate a slight increase in affinity of the monomer for binding in the homotetramer (−0.55 kcal/mol), this is likely not enough to make up for the monomer destabilization.

The 2-H2 lysate included two separate mutant EforRed polypeptides. The first mutant polypeptide included D119G and F163L substitutions. The aspartic acid in position 119 is on the surface of the protein and the loss of said surface charge upon substitution to glycine will destabilize the protein. The phenylalanine in position 163 is involved in pi-pi stacking interactions. These stacking interactions are lost upon substitution to leucine, destabilizing the protein. The homology model calculations in Table 4 estimate that the D119G and F163L substitutions destabilize the protein (22.63 kcal/mol). While the calculations also estimate a slight increase in affinity of the monomer for binding in the homotetramer (−2.3 kcal/mol), this is likely not enough to make up for the monomer destabilization.

Figure 9:
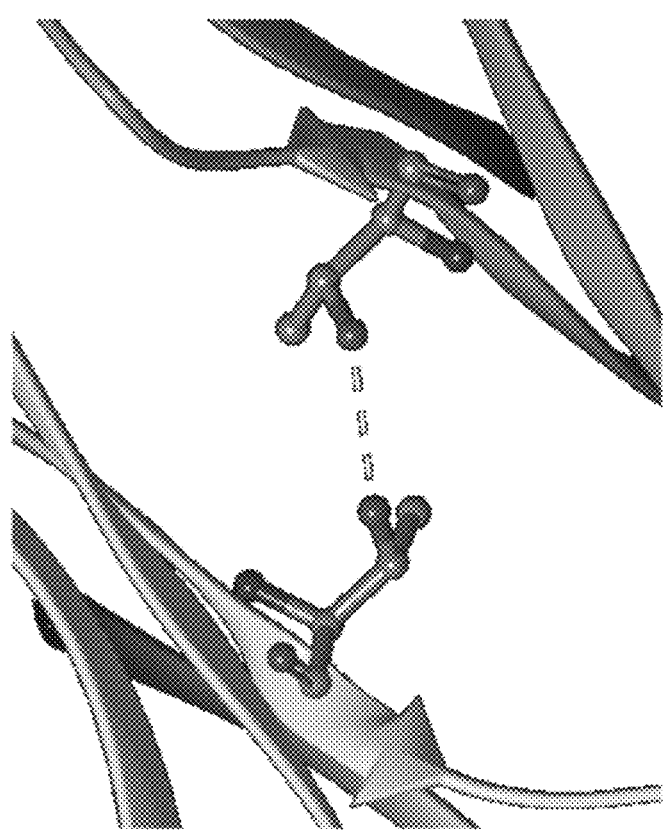
FIG. 9 shows hydrogen bonding (dotted line) between threonine 102 in one monomer and the threonine 102 in an adjacent monomer of the homotetramer. Each of the threonine residues is shown in a ball-and-stick model and the backbone of each monomer is shown as a ribbon diagram.

The second mutant EforRed polypeptide in the 2-H2 lysate includes a T102A substitution. As shown in FIG. 9, the threonine in position 102 (labeled Thr102 Chain B) hydrogens bonds (shown as a dotted line) with threonine 102 from another monomer (labeled Thr102 Chain C) in the EforRed homotetramer. This intermonomer hydrogen bond is lost when the alanine residue is present in the 102 position, which destabilizes the homotetramer. The homology model calculations in Table 4 estimate that the T102A substitution both destabilizes the protein (32.32 kcal/mol) and reduces monomer affinity (17.11 kcal/mol).

The invention claimed is:

1. A thermolabile red chromogenic protein (RCP) polypeptide comprising a sequence at least 80% identical to SEQ ID NO: 1 and comprising an XYG chromophore tripeptide and a mutation at a position selected from the group consisting of phenylalanine (F) 68, threonine (T) 102, aspartate (D) 119, D130, alanine (A) 139, F163, F206, A214, and combinations thereof relative to SEQ ID NO:1, wherein the absorbance of the thermolabile RCP polypeptide at 580 nm after heating at 80° C. for 20 minutes is decreased by at least 20% relative to the absorbance at 580 nm prior to heating.

2. The RCP of claim 1, wherein the polypeptide comprises a sequence at least 85% identical to SEQ ID NO:1.

3. The RCP of claim 1, wherein the polypeptide comprises a mutation selected from the group consisting of
(i) a tyrosine (Y) amino acid residue at position 68;
(ii) a T amino acid residue at position 214;
(iii) a glycine (G) amino acid residue at position 130;
(iv) a T amino acid residue at position 139;
(v) a serine(S) amino acid residue at position 206;
(vi) a G amino acid residue at position 119;
(vii) a leucine (L) amino acid residue at position 163;
(viii) an A amino acid residue at position 102; and
(iv) a combination thereof, all relative to SEQ ID NO:1.

4. The RCP of claim 1, wherein the polypeptide comprises a mutation selected from the group consisting of
(i) a tyrosine (Y) amino acid residue at position 68 and a T amino acid residue at position 214 relative to SEQ ID NO:1;
(ii) a glycine (G) amino acid residue at position 130 and a T amino acid residue at position 139 relative to SEQ ID NO:1;
(iii) a serine(S) amino acid residue at position 206 relative to SEQ ID NO:1;
(iv) a G amino acid residue at position 119 and a leucine (L) amino acid residue at position 163 relative to SEQ ID NO:1;
(v) an A amino acid residue at position 102 relative to SEQ ID NO:1; and
(iv) a combination thereof.

5. The RCP of claim 1, wherein the polypeptide comprises a sequence at least 80% identical to the sequence of at least one of SEQ ID NOs: 2-6.

6. A pigment composition for a meat substitute comprising the thermolabile RCP polypeptide of claim 1 in an amount effective for increasing a red color of a raw or uncooked meat substitute.

7. The composition of claim 6, wherein when the pigment is heated at 80° C. for 20 minutes absorbance at 580 nm is decreased relative to the absorbance at 580 nm prior to heating.

8. A meat substitute comprising:
the thermolabile RCP polypeptide of claim 1, and
a non-meat protein.

9. The meat substitute of claim 8, wherein a red color of the meat substitute decreases after cooking.

10. The meat substitute of claim 8, wherein the non-meat protein is a plant-based protein selected from the group consisting of pea protein, soy protein, corn protein, and wheat protein.

11. The meat substitute of claim 8, wherein the meat substitute comprises 0.01% to 6% by weight of a pigment composition comprising the thermolabile RCP polypeptide.

12. The meat substitute of claim 8, wherein the RCP polypeptide comprises a sequence at least 85% identical to SEQ ID NO:1.

13. The meat substitute of claim 8, wherein the polypeptide comprises a mutation selected from the group consisting of
(i) a Y amino acid residue at position 68;
(ii) a T amino acid residue at position 214;
(iii) a G amino acid residue at position 130;
(iv) a T amino acid residue at position 139;
(v) a S amino acid residue at position 206;
(vi) a G amino acid residue at position 119;

(vii) a L amino acid residue at position 163;
(viii) an A amino acid residue at position 102; and
(iv) a combination thereof, all relative to SEQ ID NO:1.

14. The meat substitute of claim 8 wherein the RCP polypeptide comprises a mutation selected from the group consisting of
(i) a tyrosine (Y) amino acid residue at position 68 and a T amino acid residue at position 214 relative to SEQ ID NO:1;
(ii) a glycine (G) amino acid residue at position 130 and a T amino acid residue at position 139 relative to SEQ ID NO:1;
(iii) a serine(S) amino acid residue at position 206 relative to SEQ ID NO:1;
(iv) a G amino acid residue at position 119 and a leucine (L) amino acid residue at position 163 relative to SEQ ID NO:1;
(viii) an A amino acid residue at position 102 relative to SEQ ID NO:1; and
(iv) a combination thereof.

15. The meat substitute of claim 8, wherein the RCP polypeptide comprises a sequence at least 80% identical to the sequence of at least one of SEQ ID NOs: 2-6.

16. The meat substitute of claim 8, wherein the non-meat protein is a fungal derived mycoprotein.

17. A method for decreasing red color in a cooked meat substitute, comprising:
cooking a meat substitute comprising a non-meat protein and a thermolabile RCP polypeptide comprising a sequence at least 80% identical to SEQ ID NO:1 and comprising an XYG chromophore tripeptide and a mutation at a position selected from the group consisting of F68, T102, D119, D130, A139, F163, F206, A214, and combinations thereof, relative to SEQ ID NO: 1, whereby the red color of the cooked meat substitute is reduced relative to red color of the meat substitute prior to cooking; and wherein the absorbance of the thermolabile RCP polypeptide at 580 nm after heating at 80° C. for 20 minutes is decreased by at least 20% relative to the absorbance at 580 nm prior to heating.

18. The method of claim 17, wherein when heated at 130° C. for 90 seconds the a* value of L*a*b* colorimetry of the meat substitute decreases by at least 5%.

19. A cell comprising an exogenous polynucleotide encoding a thermolabile RCP polypeptide comprising a sequence at least 80% identical to SEQ ID NO: 1 and comprising an XYG chromophore tripeptide and a mutation at a position selected from the group consisting of F68, T102, D119, D130, A139, F163, F206, A214, and combinations thereof, relative to SEQ ID NO: 1, wherein the absorbance of the thermolabile RCP polypeptide at 580 nm after heating at 80° C. for 20 minutes is decreased by at least 20% relative to the absorbance at 580 nm prior to heating.

20. The cell of claim 19, wherein the RCP polypeptide comprises a sequence at least 85% identical to SEQ ID NO:1.

21. The cell of claim 19, wherein the polypeptide comprises a mutation selected from the group consisting of
(i) a Y amino acid residue at position 68;
(ii) a T amino acid residue at position 214;
(iii) a G amino acid residue at position 130;
(iv) a T amino acid residue at position 139;
(v) a S amino acid residue at position 206;
(vi) a G amino acid residue at position 119;
(vii) a L amino acid residue at position 163;
(viii) an A amino acid residue at position 102; and
(iv) a combination thereof, all relative to SEQ ID NO:1.

22. The cell of claim 19, wherein the RCP polypeptide comprises a mutation selected from the group consisting of
(i) a tyrosine (Y) amino acid residue at position 68 and a T amino acid residue at position 214 relative to SEQ ID NO:1;
(ii) a glycine (G) amino acid residue at position 130 and a T amino acid residue at position 139 relative to SEQ ID NO:1;
(iii) a serine(S) amino acid residue at position 206 relative to SEQ ID NO:1;
(iv) a G amino acid residue at position 119 and a leucine (L) amino acid residue at position 163 relative to SEQ ID NO:1;
(v) an A amino acid residue at position 102 relative to SEQ ID NO:1; and
(iv) a combination thereof.

23. The cell of claim 19, wherein the RCP polypeptide comprises a sequence at least 80% identical to the sequence of at least one of SEQ ID NOs: 2-6.

24. The cell of claim 19, wherein the cell is a plant cell.
25. The cell of claim 19, wherein the cell is a fungal cell.
26. The cell of claim 19, wherein the cell is an animal cell.
27. The cell of claim 26, wherein the cell is an insect cell.
28. The cell of claim 26, wherein the cell is an in vitro cultured mammalian or avian cell.
29. A meat substitute comprising the cell of claim 19.

* * * * *

```
                              SEQUENCE LISTING

Sequence total quantity: 8
SEQ ID NO: 1            moltype = AA  length = 227
FEATURE                 Location/Qualifiers
source                  1..227
                        mol_type = protein
                        organism = Echinopora forskaliana
SEQUENCE: 1
MSVIKQVMKT KLHLEGTVNG HDFTIEGKGE GKPYEGLQHM KMTVTKGAPL PFSVHILTPS   60
HMYGSKPFNK YPADIPDYHK QSFPEGMSWE RSMIFEDGGV CTASNHSSIN LQENCFIYDV  120
KFHGVNLPPD GPVMQKTIAG WEPSVETLYV RDGMLKSDTA MVFKLKGGGH HRVDFKTTYK  180
AKKPVKLPEF HFVEHRLELT KHDKDFTTWD QQEAAEGHFS PLPKALP              227

SEQ ID NO: 2            moltype = AA  length = 227
FEATURE                 Location/Qualifiers
source                  1..227
                        mol_type = protein
                        organism = synthetic construct
SEQUENCE: 2
MSVIKQVMKT KLHLEGTVNG HDFTIEGKGE GKPYEGLQHM KMTVTKGAPL PFSVHILTPS   60
HMYGSKPFNK YPADIPDYHK QSFPEGMSWE RSMIFEDGGV CTASNHSSIN LQENCFIYDV  120
KFHGVNLPPD GPVMQKTIAG WEPSVETLYV RDGMLKSDTA MVFKLKGGGH HRVDFKTTYK  180
AKKPVKLPEF HFVEHRLELT KHDKDFTTWD QQETAEGHFS PLPKALP              227

SEQ ID NO: 3            moltype = AA  length = 227
FEATURE                 Location/Qualifiers
source                  1..227
                        mol_type = protein
                        organism = synthetic construct
SEQUENCE: 3
MSVIKQVMKT KLHLEGTVNG HDFTIEGKGE GKPYEGLQHM KMTVTKGAPL PFSVHILTPS   60
HMYGSKPFNK YPADIPDYHK QSFPEGMSWE RSMIFEDGGV CTASNHSSIN LQENCFIYDV  120
KFHGVNLPPG GPVMQKTITG WEPSVETLYV RDGMLKSDTA MVFKLKGGGH HRVDFKTTYK  180
AKKPVKLPEF HFVEHRLELT KHDKDFTTWD QQEAAEGHFS PLPKALP              227

SEQ ID NO: 4            moltype = AA  length = 227
FEATURE                 Location/Qualifiers
source                  1..227
                        mol_type = protein
                        organism = synthetic construct
SEQUENCE: 4
MSVIKQVMKT KLHLEGTVNG HDFTIEGKGE GKPYEGLQHM KMTVTKGAPL PFSVHILTPS   60
HMYGSKPFNK YPADIPDYHK QSFPEGMSWE RSMIFEDGGV CTASNHSSIN LQENCFIYDV  120
KFHGVNLPPD GPVMQKTIAG WEPSVETLYV RDGMLKSDTA MVFKLKGGGH HRVDFKTTYK  180
AKKPVKLPEF HFVEHRLELT KHDKDSTTWD QQEAAEGHFS PLPKALP              227

SEQ ID NO: 5            moltype = AA  length = 227
FEATURE                 Location/Qualifiers
source                  1..227
                        mol_type = protein
                        organism = synthetic construct
SEQUENCE: 5
MSVIKQVMKT KLHLEGTVNG HDFTIEGKGE GKPYEGLQHM KMTVTKGAPL PFSVHILTPS   60
HMYGSKPFNK YPADIPDYHK QSFPEGMSWE RSMIFEDGGV CTASNHSSIN LQENCFIYDV  120
KFHGVNLPPD GPVMQKTIAG WEPSVETLYV RDGMLKSDTA MVLKLKGGGH HRVDFKTTYK  180
```

```
AKKPVKLPEF HFVEHRLELT KHDKDFTTWD QQEAAEGHFS PLPKALP                      227

SEQ ID NO: 6            moltype = AA  length = 227
FEATURE                 Location/Qualifiers
source                  1..227
                        mol_type = protein
                        organism = synthetic construct
SEQUENCE: 6
MSVIKQVMKT KLHLEGTVNG HDFTIEGKGE GKPYEGLQHM KMTVTKGAPL PFSVHILTPS        60
HMYGSKPFNK YPADIPDYHK QSFPEGMSWE RSMIFEDGGV CAASNHSSIN LQENCFIYGV        120
KFHGVNLPPD GPVMQKTIAG WEPSVETLYV RDGMLKSDTA MVFKLKGGGH HRVDFKTTYK        180
AKKPVKLPEF HFVEHRLELT KHDKDFTTWD QQEAAEGHFS PLPKALP                      227

SEQ ID NO: 7            moltype = AA  length = 162
FEATURE                 Location/Qualifiers
source                  1..162
                        mol_type = protein
                        organism = synthetic construct
SEQUENCE: 7
MSVIKQVMKT KLHLEGTVNG HDFTIEGKGE GKPYEGLQHM KMTVTKGAPL PFSVHILTPS        60
HMYGSKPFNK YPADIPDYHK QSFPEGMSWE RSMIFEDGGV CTASNHSSIN LQENCFIYDV        120
KFHGVNLPPD GPVMQKTIAG WEPSVETLYV RDGMLKSDTA MV                          162

SEQ ID NO: 8            moltype = AA  length = 20
FEATURE                 Location/Qualifiers
source                  1..20
                        mol_type = protein
                        organism = synthetic construct
SEQUENCE: 8
MGSSHHHHHH SSGLVPRGSH                                                   20
```